(12) United States Patent
Holcombe et al.

(10) Patent No.: US 12,427,472 B2
(45) Date of Patent: Sep. 30, 2025

(54) PROCESS FOR REMOVAL OF ACID GASES FROM A FLUID STREAM

(71) Applicant: BASF SE, Ludwigshafen am Rhein (DE)

(72) Inventors: Thomas Wesley Holcombe, Ludwigshafen am Rhein (DE); Thomas Ingram, Ludwigshafen am Rhein (DE); Alexander Panchenko, Ludwigshafen am Rhein (DE); Martin Ernst, Ludwigshafen am Rhein (DE); Georg Sieder, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 383 days.

(21) Appl. No.: 17/641,845

(22) PCT Filed: Aug. 31, 2020

(86) PCT No.: PCT/EP2020/074181
§ 371 (c)(1),
(2) Date: Mar. 10, 2022

(87) PCT Pub. No.: WO2021/047928
PCT Pub. Date: Mar. 18, 2021

(65) Prior Publication Data
US 2024/0042375 A1   Feb. 8, 2024

(30) Foreign Application Priority Data

Sep. 10, 2019   (EP) .................................... 19196362

(51) Int. Cl.
*B01D 53/14*   (2006.01)
*B01D 53/52*   (2006.01)
(Continued)

(52) U.S. Cl.
CPC ..... *B01D 53/1493* (2013.01); *B01D 53/1425* (2013.01); *B01D 53/1468* (2013.01);
(Continued)

(58) Field of Classification Search
CPC ............ B01D 53/1493; B01D 53/1425; B01D 53/1468; B01D 53/52; B01D 53/78;
(Continued)

(56) References Cited

U.S. PATENT DOCUMENTS

| 4,487,967 A | 12/1984 | Stogryn et al. |
| 4,537,753 A | 8/1985 | Wagner et al. |

(Continued)

FOREIGN PATENT DOCUMENTS

| EP | 0121109 A2 | 10/1984 |
| EP | 0159495 A2 | 10/1985 |

(Continued)

OTHER PUBLICATIONS

International Search Report and Written Opinion received for PCT Patent Application No. PCT/EP2020/074181, mailed on Jan. 18, 2021, 13 pages.

(Continued)

*Primary Examiner* — Jennifer Dieterle
(74) *Attorney, Agent, or Firm* — Faegre Drinker Biddle & Reath LLP

(57) ABSTRACT

A process for removing acid gases from a fluid stream, wherein the fluid stream is contacted with an absorbent to obtain a treated fluid stream and a laden absorbent, the absorbent comprising at least one diluent and a compound of the general formula (I) wherein R1 is $C_1$-$C_3$-alkyl; R2 is $C_1$-$C_3$-alkyl; R3 is selected from hydrogen and C1-C3-alkyl; R4 is selected from hydrogen and $C_1$-$C_3$-alkyl and n is an integer in the range of 1 to 4.

11 Claims, 1 Drawing Sheet

Process for Removal of Acid Gases from a Fluid Stream

(51) Int. Cl.
*B01D 53/78* (2006.01)
*B01D 53/96* (2006.01)
*C07C 319/20* (2006.01)

(52) U.S. Cl.
CPC .............. *B01D 53/52* (2013.01); *B01D 53/78* (2013.01); *B01D 53/96* (2013.01); *C07C 319/20* (2013.01); *B01D 2252/20405* (2013.01); *B01D 2252/20484* (2013.01); *B01D 2252/602* (2013.01); *B01D 2257/304* (2013.01)

(58) Field of Classification Search
CPC .......... B01D 53/96; B01D 2252/20405; B01D 2252/20484; B01D 2252/602; B01D 2257/304; B01D 53/14; B01D 2252/20489; B01D 2252/20426; B01D 2252/20431; B01D 53/1462; B01D 2257/504; B01D 53/48; B01D 2252/20478; B01D 2256/245; B01D 2257/302; B01D 2257/306; B01D 2257/308; B01D 2257/408; C07C 319/20; C07C 323/12; C07C 319/14; C07C 323/25; Y02C 20/40; Y02P 20/151
USPC .............................................. 95/36
See application file for complete search history.

(56) References Cited

U.S. PATENT DOCUMENTS

| | | |
|---|---|---|
| 4,553,984 A | 11/1985 | Volkamer et al. |
| 4,665,195 A | 5/1987 | Stogryn et al. |
| 4,894,178 A | 1/1990 | Ho et al. |
| 2007/0264180 A1* | 11/2007 | Carrette .............. B01D 53/1425 423/228 |
| 2007/0286783 A1* | 12/2007 | Carrette .............. B01D 53/1425 423/220 |
| 2010/0037775 A1 | 2/2010 | Siskin et al. |
| 2013/0011314 A1 | 1/2013 | Porcheron et al. |
| 2015/0027055 A1 | 1/2015 | Kortunov et al. |
| 2017/0320008 A1 | 11/2017 | Weiss et al. |
| 2019/0381448 A1* | 12/2019 | Ingram .............. B01D 53/1456 |

FOREIGN PATENT DOCUMENTS

| | | |
|---|---|---|
| EP | 0190434 A2 | 8/1986 |
| EP | 0202600 A2 | 11/1986 |
| EP | 0359991 A1 | 3/1990 |
| EP | 2283911 A1 | 2/2011 |
| WO | 01/00271 A1 | 1/2001 |
| WO | 2011/067199 A1 | 6/2011 |
| WO | 2013/181245 A1 | 12/2013 |
| WO | 2014/001664 A1 | 1/2014 |
| WO | 2015/007970 A1 | 1/2015 |
| WO | 2017/186466 A1 | 11/2017 |
| WO | 2018/146233 A1 | 8/2018 |
| WO | 2019/043099 A1 | 3/2019 |

OTHER PUBLICATIONS

European Search Report for EP Patent Application No. 19196362.8, Issued on Oct. 15, 2020, 3 pages.
International Preliminary Report on Patentability received for PCT Patent Application No. PCT/EP2020/074181, mailed on Mar. 24, 2022, 11 pages.

* cited by examiner

Process for Removal of Acid Gases from a Fluid Stream
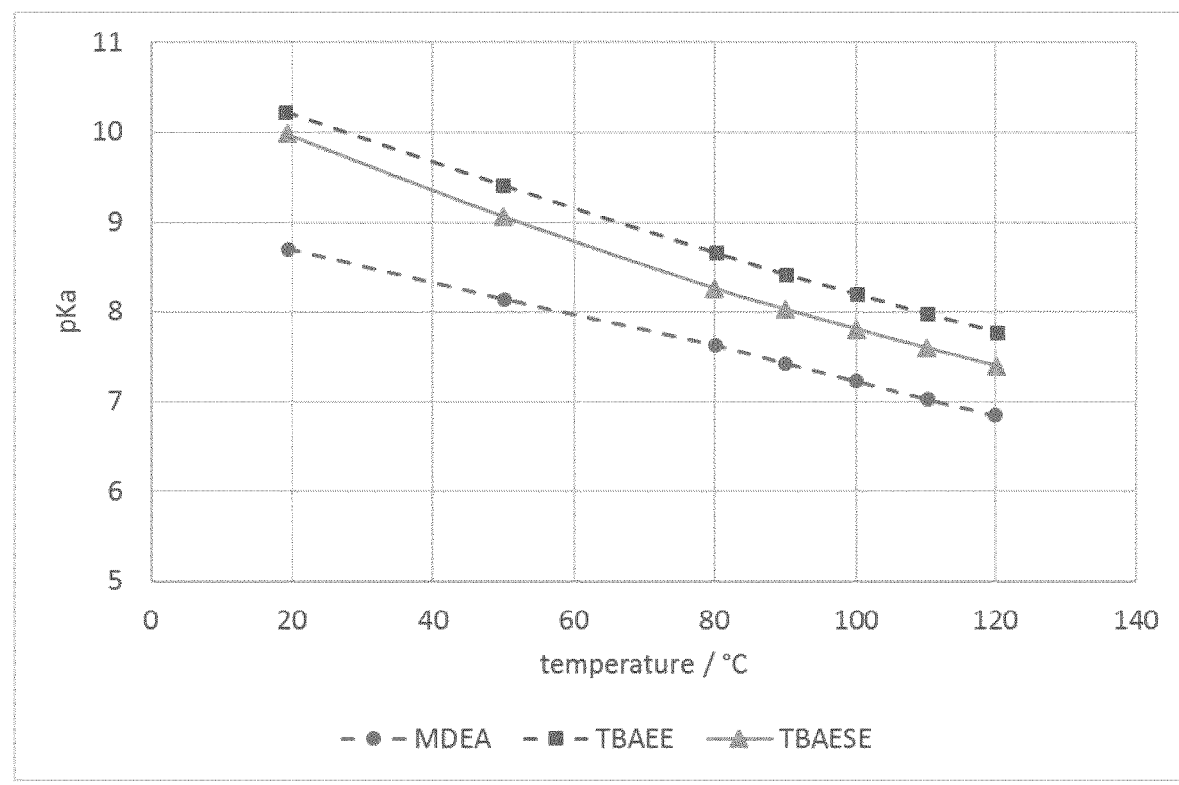

PROCESS FOR REMOVAL OF ACID GASES FROM A FLUID STREAM

CROSS-REFERENCE TO RELATED APPLICATIONS

This application is a national stage application (under 35 U.S.C. § 371) of PCT/EP2020/074181, filed Aug. 31, 2020, which claims benefit of European Application No. 19196362.8, filed Sep. 10, 2019, both of which are incorporated herein by reference in their entirety.

The present invention relates to the use of an absorbent and to a process for removing acid gases from a fluid stream. In certain embodiments, the present invention relates to the selective removal of hydrogen sulfide from a fluid stream comprising carbon dioxide and hydrogen sulfide.

The removal of acid gases, for example $CO_2$, $H_2S$, $SO_2$, $CS_2$, HCN, COS or mercaptans, from fluid streams such as natural gas, refinery gas or synthesis gas is desirable for various reasons. Sulfur compounds in natural gas tend to form corrosive acids, in particular together with the water frequently entrained by the natural gas. For the transport of the natural gas in a pipeline or further processing in a natural gas liquefaction plant (LNG=liquefied natural gas), given limits for the sulfur-containing impurities therefore must be observed. In addition, numerous sulfur compounds are malodorous and toxic even at low concentrations.

Carbon dioxide has to be removed from natural gas because a high concentration of $CO_2$ reduces the calorific value of the gas. Moreover, $CO_2$ in conjunction with moisture can lead to corrosion in pipes and valves.

Known processes for removing acid gases include scrubbing operations with aqueous absorbent solutions of inorganic or organic bases. When acid gases are dissolved in the absorbent, ions form with the bases. The absorbent can be regenerated by decompression to a lower pressure and/or by stripping, whereby the ionic species react in reverse and the acid gases are released and/or stripped out by means of an inert fluid, e.g., steam. After the regeneration process, the absorbent can be reused.

A process in which $CO_2$ and $H_2S$ are substantially removed is referred to as "total absorption". While removal of $CO_2$ may be necessary to avoid corrosion problems and provide the required heating value to the consumer, it is occasionally necessary or desirable to treat acid gas mixtures containing both $CO_2$ and $H_2S$ to remove the $H_2S$ selectively from the mixture while minimizing removal of the $CO_2$. Natural gas pipeline specifications, for example, set more stringent limits on the $H_2S$ level than on $CO_2$ since $H_2S$ is more toxic and corrosive than $CO_2$. Common carrier natural gas pipeline specifications typically limit the $H_2S$ content to 4 ppmv with a more lenient limitation on the $CO_2$ at 2 vol %. Selective $H_2S$ removal is often desirable to enrich the $H_2S$ level in the feed to a sulfur recovery, such as a downstream Claus plant.

Severely sterically hindered secondary amines, such as 2-(2-tertbutylaminoethoxy) ethanol (TBAEE), and tertiary amines, such as methyldiethanolamine (M DEA), exhibit kinetic selectivity for $H_2S$ over $CO_2$. Such amines are therefore suitable for the selective removal of $H_2S$ over $CO_2$ from gas mixtures comprising $CO_2$ and $H_2S$ and are generally utilized as aqueous mixtures. These amines do not react directly with $CO_2$; instead, $CO_2$ is reacted in a slow reaction with the amine and with water to give a bicarbonate ion. The reaction kinetics allow $H_2S$ to react directly, more rapidly, with the amine groups of the sorbent to form a hydrosulfide ion in aqueous solution.

The use of hydroxyl-substituted amines (alkanolamines) such as those mentioned above has become common since the presence of the hydroxyl groups tends to improve the solubility of the absorbent and its acid gas reaction products in the widely used aqueous solvent systems, so facilitating circulation of the solvent through the conventional absorber tower/regeneration tower unit by suppressing phase separation. The presence of the hydroxyl groups also can reduce the volatility of the amine and, consequently, reduce amine losses during operation.

This preference may, however, present its own problems in certain circumstances.

While the alkanolamines will effectively remove acid gases at higher pressures, the selectivity for $H_2S$ removal can be expected to decrease markedly both by direct physical absorption of the $CO_2$ in the liquid solvent and by reaction with the hydroxyl groups with the amine compound. Although the $CO_2$ reacts preferentially with the amino nitrogen, higher pressures force reaction with the oxygens and under the higher pressures, the bicarbonate/hemicarbonate/carbonate reaction product(s) formed by the reaction at the hydroxyl site is stabilized with a progressive loss in $H_2S$ selectivity with increasing pressure.

Further, while the presence of the hydroxyl groups improves the aqueous solubility of the amines, hydroxyl groups tend to impart surfactant properties to the absorbent/acid gas reaction products, thereby potentially causing troublesome foaming phenomena during the operation of the gas treatment unit.

Another known problem of using aqueous amine mixtures in the absorption treatment of gas mixtures is that separation into several phases may occur at temperatures falling within the range of regeneration temperatures for the aqueous amine mixtures, which is usually in the range of 50° C. to 170° C.

U.S. Pat. Nos. 4,487,967, 4,665,195 and 4,894,178 relate to a process of preparing sterically hindered aminoether alcohols, or di-amino-polyalkylene ethers, in the presence of a hydrogenation catalyst.

US 2015/0027055 describes a process for selectively removing $H_2S$ from a $CO_2$-containing gas mixture by means of an absorbent comprising sterically hindered, terminally etherified alkanolamines. It was found that the terminal etherification of the alkanolamines and the exclusion of water permits a higher $H_2S$ selectivity.

US 2010/0037775 describes an acid gas absorbent comprising an alkylamino alkyloxy (alcohol) monoalkyl ether and a process for the selective removal of $H_2S$ from gaseous mixtures containing $H_2S$ and $CO_2$ using an absorbent solution comprising said monoalkyl ether.

WO 2013/181245 describes an absorbent composition useful in the selective removal of $H_2S$, wherein the absorbent composition includes an aqueous amine mixture of an amination reaction product of tert-butyl amine and a polyethylene glycol mixture, as well as an organic co-solvent, selected from sulfones, sulfone derivatives, and sulfoxides, and a strong acid to inhibit phase separation.

WO 2014/001664 discloses absorbent solutions made from tertiary diamines belonging to the hindered aminoethyl morpholine family. These compounds comprise only tertiary amino groups, which each feature a basic nitrogen atom.

US 2013/011314 describes compounds containing one or more diamines whose two amine functions are not connected to each other by rings and whose amine function in the α-position is always tertiary and the amine function in the w-position is always either primary or secondary and the use of such compounds in the selective removal of $H_2S$ from a gas containing $H_2S$ and $CO_2$. The compounds described therein feature a secondary amino group and a tertiary amino group, both of which feature a basic nitrogen atom.

WO 2017/186466 discloses a process for the removal of acid gases from a fluid stream with morpholine-based hindered amine compounds.

WO 2018/146233 describes a process for the removal of acid gases from a fluid stream obtained from the reaction of glycidol derivatives with sterically hindered amines, such as tert-butylamine.

WO 2019/043099 is directed to absorbent solutions derived from the reaction of tert-butylamine with hydroxyethylpyrrolidone and structurally related compounds and their use in gas treating.

US 2017/0320008 discloses a process for the selective removal of $H_2S$ from a gaseous mixture comprising both $H_2S$ and $CO_2$ by contacting the mixture with an absorbent comprising an amine, water and at least one $C_{1-4}$-thioalcohol. The disclosed process has a high selectivity for the removal of $H_2S$ and also allows for improved removal of other sulfur components, in particular mercaptans.

BRIEF DESCRIPTION OF THE DRAWINGS

FIG. 1 is a graph of the $pK_a$-values for TBAESE and TBAEE measured in the temperature range between 20° C. and 120° C. as described in Example 2 of the present disclosure.

It is an object of the invention to provide further processes suitable for removing acid gases from fluid streams. The processes are to be useful for applications in total absorption, where $CO_2$ and $H_2S$ are substantially removed, as well as for the selective removal of hydrogen sulfide from fluid streams. The absorbents used in the process are to have a high cyclic capacity and a low volatility. A further object of the present invention was to provide a gas treating process based on solvents with an enhanced thermal stability which can be operated a higher temperatures over longer period of times. A further object of the invention was to provide a gas treating process with a high selectivity for the removal of $H_2S$ from gaseous mixtures comprising both $H_2S$ and $CO_2$ which also allows for the removal of other sulfur components which may be additionally comprised in gaseous mixtures comprising both $H_2S$ and $CO_2$. In particularly, the process of the present invention should also allow for the removal of mercaptans in such a selective gas treatment process.

The object is achieved by
 a process for removing acid gases from a fluid stream, wherein the fluid stream is contacted with an absorbent to obtain a treated fluid stream and a laden absorbent, the absorbent comprising at least one diluent and a compound of the general formula (I)

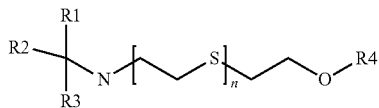

wherein R1 is $C_1$-$C_3$-alkyl; R2 is $C_1$-$C_3$-alkyl; R3 is selected from hydrogen and $C_1$-$C_3$-alkyl; R4 is selected from hydrogen and $C_1$-$C_3$-alkyl and n is an integer in the range of 1 to 4.

Compounds of the general formula (I) are based on thiodiglycol and its derivates and comprise a thioether functionality. Compared to gas treating solvents of the prior art which comprise oxyether functionalities, it was surprisingly found that gas treating process using solvents comprising compounds of formula (I) exhibit a higher thermal stability while maintaining favorable absorption properties.

Absorbent:

The process according to the invention is conducted in the presence of an absorbent.

The absorbent comprises a compound of formula (I) and at least one diluent.

Compound of Formula (I):

The absorbent comprises a compound of formula (I).

In formula (I),
 R1 is $C_1$-$C_3$-alkyl, preferably methyl, ethyl, propyl and iso-propyl and most preferably methyl; R2 is $C_1$-$C_3$-alkyl; preferably methyl, ethyl, propyl and iso-propyl and most preferably methyl;
 R3 is selected from hydrogen and $C_1$-$C_3$-alkyl, preferably methyl, ethyl, propyl and iso-propyl and most preferably methyl;
 R4 is selected from hydrogen and $C_1$-$C_3$-alkyl, preferably methyl, ethyl, propyl and iso-propyl and most preferably methyl; and
 Is an integer in the range of 1 to 4, preferably 1 or 2, and most preferably 1.

In preferred embodiments, R1 and R2 are methyl and R3 is hydrogen; or R1, R2 and R3 are methyl; or R1 and R2 are methyl and R3 is ethyl. In an especially preferred embodiment, R1, R2 and R3 are methyl.

In a preferred embodiment, the compound of general formula (I) is selected from
 2-[2-(tert-butylamino)ethylsulfanyl]ethanol; or
 N-[2-(2-methoxyethylsulfanyl)ethyl]-2-methyl-propan-2-amine; or
 N-[2-(2-ethoxyethylsulfanyl)ethyl]-2-methyl-propan-2-amine; or
 2-[2-(isopropylamino)ethylsulfanyl]ethanol; or
 N-[2-(2-methoxyethylsulfanyl)ethyl]propan-2-amine; or
 N-[2-(2-ethoxyethylsulfanyl)ethyl]propan-2-amine.

In the most preferred embodiment, the compound of general formula (I) is 2-[2-(tert-butylamino)ethylsulfanyl]ethanol.

The absorbent comprises preferably 10% to 70% by weight, more preferably 15% to 65% by weight and most preferably 20% to 60% by weight of a compound of the general formula (I), based on the total weight of the absorbent.

Synthesis of Compounds of Formula (I):

The compounds of formula (I) are commercially available or can be prepared in various ways.

In a preferred embodiment a compound of formula (I) is prepared by converting an amine of formula (II)

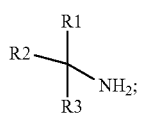

wherein R1 is $C_1$-$C_3$-alkyl; R2 is $C_1$-$C_3$-alkyl; R3 is selected from hydrogen and $C_1$-$C_3$-alkyl;
 with an alcohol of formula (III)

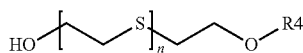

wherein R4 is selected from hydrogen and $C_1$-$C_3$-alkyl; and n is an integer in the range of 1 to 4;

in the liquid phase and in the presence of a catalyst.

Preferably, the amine of formula (II) is tert-butylamine or iso-propylamine. Most preferably, the amine of formula (II) is tert-butylamine.

The alcohol of formula (III) is preferably 2-(2-hydroxyethylsulfanyl)ethanol (thiodiglycol), or 2-(2-methoxyethylsulfanyl)ethanol, or 2-(2-ethoxyethylsulfanyl)ethanol.

In the most preferred embodiment, the amine of formula (II) is tert-butylamine and the alcohol of formula (III) is thiodiglycol.

In a further embodiment, n is equal to 3 or 4 and R4 is methyl.

Preferably, the molar ratio of amine of formula (II) to alcohol of formula (111) is in the range of 0.8:1 to 1.2:1, more preferably 0.9:1 to 1.1:1 and most preferably 1:1.

Preferably, the reaction is preferably carried out in the presence of a hydrogenation/dehydrogenation catalyst.

The catalysts may in principle comprise nickel, cobalt, iron, copper, chromium, manganese, copper, molybdenum, tungsten and/or other metals of groups 8 and/or 9 and/or 10 and/or 11 of the periodic table of the elements Preference is given to using catalysts which comprise at least one metal selected from the group consisting of Cu, Co, Ni, Pd, Pt, Ru, Rh, Ag, Au, Re and Ir.

More preference is given to using catalysts which comprise at least one metal selected from the group consisting of Cu, Co, Ni, Pd, Pt and Ru.

The abovementioned catalysts can be doped in a customary manner with promoters, for example with chromium, iron, cobalt, manganese, molybdenum, titanium, tin, metals of the alkali metal group, metals of the alkaline earth metal group and/or phosphorus.

The catalyst can be a supported or unsupported catalyst.

Suitable support materials are carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

In a preferred embodiment of the invention, catalysts of the Raney type are being used.

As Raney catalysts, Raney cobalt catalysts, Raney nickel catalysts and/or Raney copper catalysts are preferably used. Raney cobalt catalysts are particularly preferred.

In a further preferred embodiment of the invention the catalysts are prepared by reduction of a catalyst precursor, in which the aforementioned metals are present in the form of oxygen comprising compounds, such as their oxides, carbonates or hydrogencarbonates.

The catalyst precursors can be prepared by known processes, for example by precipitation, precipitative application or impregnation.

In one particularly preferred embodiment, a supported copper-, nickel- and cobalt-containing hydrogenation/dehydrogenation catalyst is used, wherein the catalytically active material of the catalyst, before the reduction thereof with hydrogen, comprises oxygen compounds of aluminum, of copper, of nickel and of cobalt, and in the range from 0.2 to 5.0% by weight of oxygen compounds of tin, calculated as SnO. In a preferred embodiment, a catalyst according to the catalysts claimed in WO 2011/067199 is used.

In a preferred embodiment, the reaction is carried out at a temperature of 150 to 260° C. In an especially preferred embodiment, the reaction is carried out at a temperature of 170 to 240° C. In a most preferred embodiment, the reaction is carried out at a temperature of 180 to 220° C.

The reaction may be carried out at pressures from 5 to 300 bar. In a preferred embodiment, the reaction is carried out at a pressure of 50 to 200 bar (abs.). In an especially preferred embodiment, the reaction is carried out at a pressure of 60 to 130 bar (abs.).

The conversion of the amine of formula (II) and the alcohol of formula (III) is preferably conducted in the liquid phase. Within the meaning of the present invention, the conversion is conducted in the liquid phase if either the amine of formula (II), the alcohol of formula (III) or the solvent is in the liquid phase under the conditions of the reaction.

The conversion is preferably carried out in the presence of hydrogen. During the reaction, hydrogen is not consumed but has beneficial effects on maintaining the catalyst activity. The partial pressure of hydrogen is preferably in the range of 2.5 to 200 bar, more preferably in the range of 5 to 150 bar, even more preferably in the range of 10 to 100 bar and most preferably in the range of 20 to 50 bar.

The conversion can be carried out in the presence of a solvent. The solvent used may be any solvent which is inert under the reaction conditions and has a sufficient solubility for the reactants and reaction products. Useful solvents do not comprise functional groups, which can react with the amine of formula (II) under the conditions of the amination reaction, e.g. hydroxyl groups. Preferably the one or more solvents are water, ethers, preferably methyl tert-butyl ether, ethyl tert-butyl ether, dioxane, tetrahydrofuran (THF), proglyme, diglyme, polyglymes and generally diethers of oligo- and polypropyleneoxides and oligo- and polyethyleneoxides or mixed oligo- or polyalkyleneoxides.

Useful solvents also include suitable mixtures of the solvents listed above.

Particularly preferred solvents are glymes, THF and water.

The amount of solvent present in the reaction mixture is usually in the range of 1 to 95% by weight, preferably 2.5 to 70%, more preferably 5 to 40%, based on the total weight of the reaction mixture, where the total weight of the reaction mixture is composed of the sum of the masses of all components added to the conversion of the amine of formula (II), i.e. amine of formula (II) and the alcohol of formula (III) and the solvents.

The reaction may be carried out using stirred tank reactors, fixed bed tube reactors and multitube reactors. It may be carried out in batch, semi-batch and continuous mode and with and without recycling of the crude reaction mixture. In a preferred embodiment, the reaction is carried out in continuous mode in a fixed bed tube reactor.

The catalyst load may be varied in the range of 0.01 to 2 kg/(L-h), preferably in the range of 0.1 to 1.0 kg/(L-h), and in an especially preferred embodiment in the range of 0.2 to 0.8 kg/(L-h) of ether of formula (II).

The reaction product comprises unreacted amine of formula (II), alcohol of formula (III) and the compound of formula (III).

The reaction product is preferably refined by conduction one or more distillation steps.

On a laboratory scale, compounds of formula (I) may also be obtained by reaction of compounds of formula (IV)

(IV)

wherein R4 is selected from hydrogen and $C_1$-$C_3$-alkyl; and n is an integer in the range of 1 to 4, and 2-chloro-N-tert-butylethylamin hydrochloride in the presence of sodium ethanolate.

In a typical laboratory synthesis, the compound of formula (IV) is dissolved in a 10 wt.-% solution of sodium methylate in ethanol. The 2-chloro-N-tert-butylethylamin is usually added as a 5 to 10 wt.-% solution in ethanol. The mixing is usually conducted in a manner so that the temperature of the resulting mixture is maintained in a range of 35 to 40° C., To complete the reaction, the resulting reaction mixture is typically stirred at 75° C. for 90 minutes for another 6 to 12 hours at room temperature.

Preferably, the reaction is conducted under inert conditions, such as nitrogen atmosphere and using dried solvents. The resulting suspension is usually filtered through a laboratory filter and the filtrate is evaporated in a rotary evaporator to remove ethanol obtain the desired products.

Diluent:

The compound of the general formula (I) is diluted with a diluent, preferably a low-cost diluent. The diluent may be one that has only physical absorptivity for carbon dioxide and other constituents of the gas such as $H_2S$. Preferably, however, the diluent interacts with the acid-base chemistry of the process. In particular, the diluent is an aqueous diluent. Due to their steric hindrance, the compounds of the general formula (I) have no sufficiently nucleophilic amine site for a direct nucleophilic attack at the $CO_2$ molecule. Thus, the water oxygen acts as the nucleophile forming a Brönsted acid, $H_2CO_3$, which is neutralized by the compound of the general formula (I) acting as a Brönsted base to form an ammonium bicarbonate.

In the most preferred embodiment, the diluent is water.

Activator:

In a preferred embodiment, the absorbent comprises at least one activator selected from a sterically unhindered primary amine and/or a sterically unhindered secondary amine. A sterically unhindered primary amine is understood to mean compounds having primary amino groups to which only a primary or a secondary carbon atom is bonded. A sterically unhindered secondary amine is understood to mean compounds having secondary amino groups to which only primary carbon atoms are bonded. Sterically unhindered primary amines or sterically unhindered secondary amines act as strong activators of $CO_2$ absorption. Accordingly, the presence of an activator may be desirable in applications directed at the non-selective removal of acid gases or applications in which the removal of $CO_2$ is especially important.

The activator preferably does not comprise acidic groups such as, in particular, phosphonic acid, sulfonic acid and/or carboxylic acid groups.

The activator is, for example, selected from:

alkanolamines such as monoethanolamine (MEA), diethanolamine (DEA), ethylaminoethanol, 1-amino-2-methylpropan-2-ol, 2-amino-1-butanol, 2-(2-aminoethoxy)ethanol and 2-(2-aminoethoxy)ethanamine, polyamines such as hexamethylenediamine, 1,4-diaminobutane, 1,3-diaminopropane, 3-(methylamino) propylamine (MAPA), N-(2-hydroxyethyl)ethylenediamine, 3-(dimethylamino) propylamine (DMAPA), 3-(diethylamino)propylamine, N,N'-bis(2-hydroxyethyl)ethylenediamine, 5-, 6- or 7-membered saturated heterocycles having at least one NH group in the ring, which may comprise one or two further heteroatoms selected from nitrogen and oxygen in the ring, such as piperazine, 2-methylpiperazine, N-methylpiperazine, N-ethylpiperazine, N-(2-hydroxyethyl)piperazine, N-(2-aminoethyl)piperazine, homopiperazine, piperidine and morpholine.

Particular preference is given to 5-, 6- or 7-membered saturated heterocycles having at least one NH group in the ring, which may comprise one or two further heteroatoms selected from nitrogen and oxygen in the ring. Very particular preference is given to piperazine.

In this preferred embodiment wherein the absorbent comprises an activator, the absorbent comprises preferably 10% to 70% by weight, more preferably 15% to 65% by weight and most preferably 20% to 60% by weight of an activator.

Absences of Sterically Unhindered Amines

In another preferred embodiment, the absorbent does not comprise any sterically unhindered primary amine or sterically unhindered secondary amine. Since sterically unhindered primary amines or sterically unhindered secondary amines act as strong activators of $CO_2$ absorption, their presence in the absorbent can result in a loss of the $H_2S$ selectivity of the absorbent. Accordingly, in applications where a high $H_2S$ selectivity is desirable, an absorbent essentially free of such compounds is preferable.

Additional Sterically Hindered Amines

In one embodiment, the absorbent comprises a tertiary amine or severely sterically hindered primary amine and/or severely sterically hindered secondary amine other than the compounds of the general formula (I). Severe steric hindrance is understood to mean a tertiary carbon atom directly adjacent to a primary or secondary nitrogen atom. In this embodiment, the absorbent comprises the tertiary amine or severely sterically hindered amine other than the compounds of the general formula (I) generally in an amount of 5% to 50% by weight, preferably 10% to 40% by weight and more preferably 20% to 40% by weight, based on the total weight of the absorbent.

1. Tertiary alkanolamines such as
    bis(2-hydroxyethyl)methylamine (methyldiethanolamine, M DEA), tris(2-hydroxyethyl)amine (triethanolamine, TEA), tributanolamine, 2-diethylaminoethanol(diethylethanolamine, DEEA), 2-dimethylaminoethanol (dimethylethanolamine, DMEA), 3-dimethylamino-1-propanol (N,N-dimethylpropanolamine), 3-diethylamino-1-propanol, 2-diisopropylaminoethanol (DIEA), N,N-bis(2-hydroxypropyl)methylamine (methyldiisopropanolamine, MDIPA);
2. Tertiary amino ethers such as
    3-methoxypropyldimethylamine;
3. Tertiary polyamines, for example bis-tertiary diamines such as
    N,N,N',N'-tetramethylethylenediamine, N, N-diethyl-N',N'-dimethylethylenediamine, N,N,N',N'-tetraethylethylenediamine, N,N,N',N'-tetramethyl-1,3-propanediamine (TMPDA), N,N,N',N'-tetraethyl-1,3-propanediamine (TEPDA), N,N,N',N'-tetramethyl-1,6-hexanediamine, N,N-dimethyl-N',N'-diethylethylenediamine (DMDEEDA), 1-dimethylamino-2-dimethylaminoethoxyethane (bis[2-(dimethylamino)ethyl] ether), 1,4-diazabicyclo[2.2.2]octane (TEDA), tetramethyl-1,6-hexanediamine;
    and mixtures thereof.

Tertiary alkanolamines, i.e. amines having at least one hydroxyalkyl group bonded to the nitrogen atom, are generally preferred. Particular preference is given to methyldiethanolamine (MDEA).

The suitable severely sterically hindered amines (i.e. amines having a tertiary carbon atom directly adjacent to a primary or secondary nitrogen atom) other than the compounds of the general formula (I) especially include:
1. Severely sterically hindered secondary alkanolamines such as
   2-(2-tert-butylaminoethoxy)ethanol (TBAEE), 2-(2-tert-butylamino)propoxyethanol, 2-(2-tert-amylaminoethoxy)ethanol, 2-(2-(1-methyl-1-ethylpropylamino)ethoxy)ethanol, 2-(tert-butylamino)ethanol, 2-tert-butylamino-1-propanol, 3-tert-butylamino-1-propanol, 3-tert-butylamino-1-butanol, and 3-aza-2,2-dimethylhexane-1,6-diol;
2. Severely sterically hindered primary alkanolamines such as
   2-amino-2-methylpropanol (2-AMP); 2-amino-2-ethylpropanol; and 2-amino-2-propylpropanol;
3. Severely sterically hindered amino ethers such as
   1,2-bis(tert-butylaminoethoxy)ethane, bis(tert-butylaminoethyl) ether;
and mixtures thereof.

Severely sterically hindered secondary alkanolamines are generally preferred.

Particular preference is given to 2-(2-tert-butylaminoethoxy)ethanol and 2-Nmethylamino-2-methylpropan-1-ol.

Acids:

In another preferred embodiment, the absorbent is an aqueous absorbent (which means that the diluent comprises water) and the absorbent additionally comprises an acid.

The acid helps to regenerate the absorbent to low loadings and enhance the efficiency of the process. Protonation equilibria form between the acid and the compound of general formula (I). The position of the equilibria is temperature-dependent, and the equilibrium is shifted at higher temperatures toward the free oxonium ion and/or the amine salt having the lower enthalpy of protonation. At relatively low temperatures as prevail in the absorption step, the higher pH promotes acid gas absorption, whereas, at relatively high temperatures as prevail in the desorption step, the lower pH supports the release of the absorbed acid gases.

The acid preferably has a $pK_a$ of less than 6, especially less than 5, measured at 25° C. under atmospheric pressure. In the case of acids having more than one dissociation stage and accordingly more than one $pK_a$, this requirement is met where one of the $pK_a$ values is within the range specified. The acid is suitably selected from protic acids (Brönsted acids).

The acid is preferably added in such an amount that the pH of the aqueous solution measured at 120° C. is 7.9 to less than 9.5, preferably 8.0 to less than 8.8, more preferably 8.0 to less than 8.5, most preferably 8.0 to less than 8.2.

The amount of acid, in one embodiment, is 0.1% to 5.0% by weight, preferably 0.2% to 15 4.5% by weight, more preferably 0.5% to 4.0% by weight and most preferably 1.0% to 2.5% by weight, based on the total weight of the absorbent.

The acid is selected from organic and inorganic acids. Suitable organic acids comprise, for example, phosphonic acids, sulfonic acids, carboxylic acids and amino acids. In particular embodiments, the acid is a polybasic acid.

Suitable acids are, for example:
mineral acids such as hydrochloric acid, sulfuric acid, amidosulfuric acid, phosphoric acid, partial esters of phosphoric acid, for example mono- and dialkyl phosphates and mono- and diaryl phosphates such as tridecyl phosphate, dibutyl phosphate, diphenyl phosphate and bis(2-ethylhexyl) phosphate; boric acid;

carboxylic acids, for example saturated aliphatic monocarboxylic acids such as formic acid, acetic acid, propionic acid, butyric acid, isobutyric acid, valeric acid, isovaleric acid, pivalic acid, caproic acid, n-heptanoic acid, caprylic acid, 2-ethylhexanoic acid, pelargonic acid, caproic acid, neodecanoic acid, undecanoic acid, lauric acid, tridecanoic acid, myristic acid, pentadecanoic acid, palmitic acid, margaric acid, stearic acid, isostearic acid, arachic acid, behenic acid; saturated aliphatic polycarboxylic acids such as oxalic acid, malonic acid, succinic acid, glutaric acid, adipic acid, pimelic acid, suberic acid, azelaic acid, sebacic acid, dodecanedioic acid; cycloaliphatic mono- and polycarboxylic acids such as cyclohexanecarboxylic acid, hexahydrophthalic acid, tetrahydrophthalic acid, resin acids, naphthenic acids; aliphatic hydroxycarboxylic acids such as glycolic acid, lactic acid, mandelic acid, hydroxybutyric acid, tartaric acid, malic acid, citric acid; halogenated aliphatic carboxylic acids such as trichloroacetic acid or 2-chloropropionic acid; aromatic mono- and polycarboxylic acids such as benzoic acid, salicylic acid, gallic acid, the positionally isomeric toluic acids, methoxybenzoic acids, chlorobenzoic acids, nitrobenzoic acids, phthalic acid, terephthalic acid, isophthalic acid; technical carboxylic acid mixtures, for example versatic acids;

sulfonic acids such as methylsulfonic acid, butylsulfonic acid, 3-hydroxypropylsulfonic acid, sulfoacetic acid, benzenesulfonic acid, p-toluenesulfonic acid, p-xylenesulfonic acid, 4-dodecylbenzenesulfonic acid, 1-naphthalenesulfonic acid, dinonylnaphthalene-sulfonic acid and dinonylnaphthalenedisulfonic acid, trifluoromethyl- or nonafluoro-n-butylsulfonic acid, camphorsulfonic acid, 2-(4-(2-hydroxyethyl)-1-piperazinyl)-ethanesulfonic acid (HEPES);

organic phosphonic acids, for example phosphonic acids of the formula (IV)

$$R4\text{-}PO_3H \quad (IV)$$

in which R4 is $C_1$-$C_{1-18}$-alkyl optionally substituted by up to four substituents independently selected from carboxyl, carboxamido, hydroxyl and amino.

These include alkylphosphonic acids such as methylphosphonic acid, propylphosphonic acid, 2-methylpropylphosphonic acid, t-butylphosphonic acid, nbutylphosphonic acid, 2,3-dimethylbutylphosphonic acid, octylphosphonic acid; hydroxyalkylphosphonic acids such as hydroxymethylphosphonic acid, 1-hydroxy-ethylphosphonic acid, 2-hydroxyethylphosphonic acid; arylphosphonic acids such as phenylphosphonic acid, tolylphosphonic acid, xylylphosphonic acid, aminoalkylphosphonic acids such as aminomethylphosphonic acid, 1-aminoethylphosphonic acid, 1-dimethylaminoethylphosphonic acid, 2-minoethylphosphonic acid, 2-(Nmethylamino) ethylphosphonic acid, 3-aminopropylphosphonic acid, 2-aminopropylphosphonic acid, 1-aminopropylphosphonic acid, 1-aminopropyl-2-chloropropylphosphonic acid, 2-aminobutylphosphonic acid, 3-aminobutylphosphonic acid, 1-aminobutylphosphonic acid, 4-aminobutylphosphonic acid, 2-aminopentylphosphonic acid, 5-aminopentylphosphonic acid, 2-aminohexylphosphonic acid, 5-aminohexylphosphonic acid, 2-aminooctylphosphonic acid, 1-aminooctylphosphonic acid, 1-aminobutylphosphonic acid; amidoalkylphosphonic acids such as 3-hydroxymethylamino-3-oxopropylphosphonic acid; and phosphonocarboxylic acids such as 2-hydroxyphosphonoacetic acid and 2-phosphonobutane-1,2,4-tricarboxylic acid;

phosphonic acids of the formula (V)

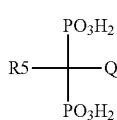

in which R5 is H or $C_{1-5}$-alkyl, Q is H, OH or $NR6_2$ and R6 is H or $CH_2PO_3H_2$, such as 1-hydroxyethane-1,1-diphosphonic acid;

phosphonic acids of the formula (VI)

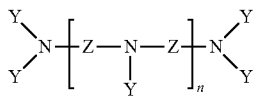

in which Z is Cm-alkylene, cycloalkanediyl, phenylene, or $C_{2-5}$-alkylene interrupted by cycloalkanediyl or phenylene, Y is $CH_2PO_3H_2$ and m is 0 to 4, such as ethylenediaminetetra(methylenephosphonic acid), diethylenetriaminepenta(methylene-phosphonic acid) and bis(hexamethylene)triaminepenta(methylenephosphonic acid);

phosphonic acids of the formula (VII)

$$R7-NY_2 \quad (VII)$$

in which R7 is $C_{1-5}$-alkyl, $C_{2-5}$-hydroxyalkyl or R8, and R8 is $CH_2PO_3H_2$, such as nitrilotris(methylenephosphonic acid) and 2-hydroxyethyliminobis(methylenephosphonic acid);

aminocarboxylic acids having tertiary amino groups or amino groups having at least one secondary or tertiary carbon atom immediately adjacent to the amino group, such as α-amino acids having tertiary amino groups or amino groups having at least one secondary or tertiary carbon atom immediately adjacent to the amino group, such as N,N-dimethylglycine (dimethylaminoacetic acid), N,N-diethylglycine, alanine (2-aminopropionic acid), N-methylalanine (2-(methylamino)propionic acid), Ndimethylalanine, N-ethylalanine, 2-methylalanine (2-aminoisobutyric acid), leucine (2-amino-4-methylpentan-1-oic acid), N-methylleucine, N,N-dimethylleucine, isoleucine (1-amino-2-methylpentanoic acid), N-methylisoleucine, N,N-dimethylisoleucine, valine (2-aminoisovaleric acid), a-methylvaline (2-amino-2-methylisovaleric acid), N-methylvaline (2-methylaminoisovaleric acid), N,N-dimethylvaline, proline (pyrrolidine-2-carboxylic acid), N-methylproline, N-methylserine, N,N-dimethylserine, 2-(methylamino) isobutyric acid, piperidine-2-carboxylic acid, N-methylpiperidine-2-carboxylic acid, ß-amino acids having tertiary amino groups or amino groups having at least one secondary or tertiary carbon atom immediately adjacent to the amino group, such as 3-dimethylaminopropionic acid, N-methyliminodipropionic acid, N-methylpiperidine-3-carboxylic acid, γ-amino acids having tertiary amino groups or amino groups having at least one secondary or tertiary carbon atom immediately adjacent to the amino group, such as 4-dimethylaminobutyric acid.

or aminocarboxylic acids having tertiary amino groups or amino groups having at least one secondary or tertiary carbon atom immediately adjacent to the amino group, such as N-methylpiperidine-4-carboxylic acid.

Among the inorganic acids, preference is given to phosphoric acid and sulfuric acid, especially sulfuric acid.

Among the carboxylic acids, preference is given to formic acid, acetic acid, benzoic acid, succinic acid and adipic acid.

Among the sulfonic acids, preference is given to methanesulfonic acid, p-toluenesulfonic acid and 2-(4-(2-hydroxyethyl)-1-piperazinyl)ethanesulfonic acid (HEPES).

Among the phosphonic acids, preference is given to 2-hydroxyphosphonoacetic acid, 2-phosphonobutane-1,2,4-tricarboxylic acid, 1-hydroxyethane-1,1-diphosphonic acid, ethylenediaminetetra(methylenephosphonic acid), diethylenetriaminepenta(methylenephosphonic acid), bis(hexamethylene)triaminepenta(methylenephosphonic acid) (HDTMP) and nitrilotris(methylenephosphonic acid), among which 1-hydroxyethane-1,1-diphosphonic acid is particularly preferred.

Among the aminocarboxylic acids having tertiary amino groups or amino groups having at least one secondary or tertiary carbon atom immediately adjacent to the amino group, preference is given to N,N-dimethylglycine and N-methylalanine.

More preferably, the acid is an inorganic acid.

Non-Aqueous Organic Solvent:

In one embodiment, the diluent of the absorbent comprises at least one non-aqueous organic solvent. In particular cases, the diluent contains only a limited amount of water, or essentially no water in addition to the non-aqueous organic solvent. It may be desirable to limit the water content of the absorbent, for example to a maximum of 20% by weight, alternatively to a maximum of 10% by weight, preferably to a maximum of 5% by weight, or a maximum of 2% by weight.

The non-aqueous organic solvent is preferably selected from:

$C_4$-$C_{10}$ alcohols such as n-butanol, n-pentanol and n-hexanol;

ketones such as cyclohexanone;

esters such as ethyl acetate and butyl acetate;

lactones such as γ-butyrolactone, o-valerolactone and ε-caprolactone;

amides such as tertiary carboxamides, for example N,N-dimethylformamide; or N-formylmorpholine and N-acetylmorpholine;

lactams such as γ-butyrolactam, o-valerolactam and ε-caprolactam and N-methyl-2-pyrrolidone (NMP);

sulfones such as sulfolane;

sulfoxides such as dimethyl sulfoxide (DMSO);

glycols such as ethylene glycol (EG) and propylene glycol;

polyalkylene glycols such as diethylene glycol (DEG) and triethylene glycol (TEG);

di- or mono($C_{1-4}$-alkyl ether) glycols such as ethylene glycol dimethyl ether;

di- or mono($C_{1-4}$-alkyl ether) polyalkylene glycols such as diethylene glycol dimethyl ether, dipropylene glycol monomethyl ether and triethylene glycol dimethyl ether;

cyclic ureas such as N,N-dimethylimidazolidin-2-one and dimethylpropyleneurea (DMPU);

thioalkanols such as ethylenedithioethanol, thiodiethylene glycol (thiodiglycol, TDG) and methylthioethanol;

and mixtures thereof.

More preferably, the non-aqueous solvent is selected from sulfones, glycols and polyalkylene glycols. Most preferably, the non-aqueous solvent is selected from sulfones. A preferred nonaqueous solvent is sulfolane.

Other Additives:

The absorbent may also comprise additives such as corrosion inhibitors, enzymes, antifoams, etc. In general, the amount of such additives is in the range from about 0.005% to 3%, based on the total weight of the absorbent.

Uses of the Absorbent:

The present invention also relates to the use of the absorbent described herein for removal of acid gases from a fluid stream.

In one embodiment, the present invention relates to the use of the absorbent described herein for the non-selective removal of acid gases from a fluid stream. In this case, it is preferred that the absorbent comprises at least one activator selected from a sterically unhindered primary amine and/or a sterically unhindered secondary amine, as described above.

In another embodiment, the present invention relates to the use of the absorbent described herein for the selective removal of hydrogen sulfide from a fluid stream comprising carbon dioxide and hydrogen sulfide. In this case, it is preferred that the absorbent does not comprise any sterically unhindered primary amine or sterically unhindered secondary amine.

In one embodiment, the process is a process for the non-selective removal of acid gases from a fluid stream. In this case, it is preferred that the absorbent comprises at least one activator selected from a sterically unhindered primary amine and/or a sterically unhindered secondary amine, as described above.

In another embodiment, the process is a process for the selective removal of hydrogen sulfide from a fluid stream comprising carbon dioxide and hydrogen sulfide. In this case, it is preferred that the absorbent does not comprise any sterically unhindered primary amine or sterically unhindered secondary amine.

In the present context, "selectivity for hydrogen sulfide" is understood to mean the value of the following quotient:

$$[mol(H_2S)/mol(CO_2)]_{liquid\ phase}/[mol(H_2S)/mol(CO_2)]_{gas\ phase}$$

where $[mol(H_2S)/mol(CO_2)]_{liquid\ phase}$ is the molar $H_2S/CO_2$ ratio in a liquid phase which is in contact with a gas phase; and $[mol(H_2S)/mol(CO_2)]_{gas\ phase}$ is the molar $H_2S/CO_2$ ratio in the gas phase.

In a standard gas scrubbing process, the liquid phase is the laden absorbent at the bottom of the absorber and the gas phase is the fluid stream to be treated.

A process is understood to be $H_2S$ selective when the value of the above quotient is greater than 1. When the process is a process for the selective removal of hydrogen sulfide from a fluid stream comprising carbon dioxide and hydrogen sulfide, the selectivity for hydrogen sulfide is preferably at least 1.1, even more preferably at least 2 and most preferably at least 4.

The absorbent described herein is suitable for treatment of all kinds of fluids. Fluids are firstly gases such as natural gas, synthesis gas, coke oven gas, cracking gas, coal gasification gas, cycle gas, landfill gases and combustion gases, and secondly liquids that are essentially immiscible with the absorbent, such as LPG (liquefied petroleum gas) or NGL (natural gas liquids). The process of the invention is particularly suitable for treatment of hydrocarbonaceous fluid streams. The hydrocarbons present are, for example, aliphatic hydrocarbons such as $C_1$-$C_4$ hydrocarbons such as methane, unsaturated hydrocarbons such as ethylene or propylene, or aromatic hydrocarbons such as benzene, toluene or xylene.

The absorbent of the invention is suitable for removal of acid gases, for example $CO_2$, $H_2S$, $SO_3$, $SO_2$, $CS_2$, HCN, COS and mercaptans. It is also possible for other acidic gases to be present in the fluid stream, such as COS and mercaptans.

The absorbent is suitable for selective removal of hydrogen sulfide from a fluid stream comprising carbon dioxide and hydrogen sulphide and allows high $H_2S$ cleanup selectively at low solvent circulation rates. The absorbent is useful in sulfur plant Tail Gas Treating Unit (TGTU) applications, in Acid-Gas Enrichment (AGE) processes to upgrade lean acid off-gas from treating units to higher-quality Claus plant feed, or for the treatment of associated gases and refinery gases.

In the process of the invention, the fluid stream is contacted with the absorbent in an absorption step in an absorber, as a result of which carbon dioxide and hydrogen sulfide are at least partly scrubbed out. This gives a $CO_2$- and $H_2S$-depleted fluid stream and a $CO_2$- and $H_2S$-laden absorbent.

The absorber used is a scrubbing apparatus used in customary gas scrubbing processes. Suitable scrubbing apparatuses are, for example, random packings, columns having structured packings and having trays, membrane contactors, radial flow scrubbers, jet scrubbers, Venturi scrubbers and rotary spray scrubbers, preferably columns having structured packings, having random packings and having trays, more preferably columns having trays and having random packings. The fluid stream is preferably treated with the absorbent in a column in countercurrent. The fluid is generally fed into the lower region and the absorbent into the upper region of the column. Installed in tray columns are sieve trays, bubble-cap trays or valve trays, over which the liquid flows. Columns having random packings can be filled with different shaped bodies. Heat and mass transfer are improved by the increase in the surface area caused by the shaped bodies, which are usually about 25 to 80 mm in size. Known examples are the Raschig ring (a hollow cylinder), Pali ring, Hiflow ring, Intalox saddle and the like. The random packings can be introduced into the column in an ordered manner, or else randomly (as a bed). Possible materials include glass, ceramic, metal and plastics. Structured packings are a further development of ordered random packings. They have a regular structure. As a result, it is possible in the case of packings to reduce pressure drops in the gas flow. There are various designs of structured packings, for example woven packings or sheet metal packings. Materials used may be metal, plastic, glass and ceramic.

The temperature of the absorbent in the absorption step is generally about 30 to 100° C., and when a column is used is, for example, 30 to 70° C. at the top of the column and 50 to 100° C. at the bottom of the column.

The process of the invention may comprise one or more, especially two, successive absorption steps. The absorption can be conducted in a plurality of successive component steps, in which case the crude gas comprising the acidic gas constituents is contacted with a substream of the absorbent in each of the component steps. The absorbent with which the crude gas is contacted may already be partly laden with acidic gases, meaning that it may, for example, be an absorbent which has been recycled from a downstream absorption step into the first absorption step, or be partly regenerated absorbent. With regard to the performance of the two-stage absorption, reference is made to publications EP 0 159 495, EP 0 190 434, EP 0 359 991 and WO 00100271.

The person skilled in the art can achieve a high level of hydrogen sulfide removal with a defined selectivity by varying the conditions in the absorption step, such as, more particularly, the absorbent/fluid stream ratio, the column height of the absorber, the type of contact-promoting internals in the absorber, such as random packings, trays or structured packings, and/or the residual loading of the regenerated absorbent. Since $CO_2$ is absorbed more slowly than $H_2S$, more $CO_2$ is absorbed in a longer residence time than in a shorter residence time. Conversely in longer residence time $H_2S$ selectivity is decreased. A higher column therefore brings about a less selective absorption. Trays or structured packings with relatively high liquid holdup likewise lead to a less selective absorption. The heating energy introduced in the regeneration can be used to adjust the residual loading of the regenerated absorbent. A lower residual loading of regenerated absorbent leads to improved absorption.

The process preferably comprises a regeneration step in which the $CO_2$- and $H_2S$-laden absorbent is regenerated. In the regeneration step, $CO_2$ and $H_2S$ and optionally further acidic gas constituents are released from the $CO_2$- and $H_2S$-laden absorbent to obtain a regenerated absorbent. Preferably, the regenerated absorbent is subsequently recycled into the absorption step. In general, the regeneration step comprises at least one of the measures of heating, decompressing and stripping with an inert fluid.

The regeneration step preferably comprises heating of the absorbent laden with the acidic gas constituents, for example by means of a boiler, natural circulation evaporator, forced circulation evaporator or forced circulation flash evaporator. The absorbed acid gases are stripped out by means of the steam obtained by heating the solution. Rather than steam, it is also possible to use an inert fluid such as nitrogen. The absolute pressure in the desorber is normally 0.1 to 3.5 bar, preferably 1.0 to 2.5 bar. The temperature is normally 50° C. to 170° C., preferably 80° C. to 130° C., the temperature of course being dependent on the pressure. In some cases, an additional regeneration step of a slip stream of the regenerated absorption solvent is needed. In the presence of $SO_x$, $NO_x$, and CO in the fluid stream heat stable salts like sulfates, nitrates, and formates can be formed. To the lower the concentration of these undesired components a further distillation step at elevated temperatures can be applied, or alternatively the heat stable salts can be removed by ion exchange process.

The regeneration step may alternatively or additionally comprise a decompression. This includes at least one decompression of the laden absorbent from a high pressure as exists in the conduction of the absorption step to a lower pressure. The decompression can be accomplished, for example, by means of a throttle valve and/or a decompression turbine. Regeneration with a decompression stage is described, for example, in publications U.S. Pat. Nos. 4,537,753 and 4,553,984.

The acidic gas constituents can be released in the regeneration step, for example, in a decompression column, for example a flash vessel installed vertically or horizontally, or a countercurrent column with internals.

The regeneration column may likewise be a column having random packings, having structured packings or having trays. The regeneration column, at the bottom, has a heater, for example a forced circulation evaporator with circulation pump. At the top, the regeneration column has an outlet for the acid gases released. Entrained absorption medium vapors are condensed in a condenser and recirculated to the column.

It is possible to connect a plurality of decompression columns in series, in which regeneration is effected at different pressures. For example, regeneration can be effected in a preliminary decompression column at a high pressure typically about 1.5 bar above the partial pressure of the acidic gas constituents in the absorption step and in a main decompression column at a low pressure, for example 1 to 2 bar absolute. Regeneration with two or more decompression stages is described in publications U.S. Pat. Nos. 4,537,753, 4,553,984, EP 0 159 495, EP 0 202 600, EP 0 190 434 and EP 0 121 109.

The process of the present invention using compounds of formula (I) show a high selectivity in the treatment of gaseous streams comprising both $H_2S$ and $CO_2$. The process of the present invention additionally allows for a high removal rate of mercaptans or other sulfur compounds which may be present in such gaseous streams. The compounds of formula (i) show a high thermal stability allowing regeneration at higher temperatures and a more complete regeneration of the absorbent solutions towards lower loading factors.

The invention is illustrated in detail by the examples which follow.

EXAMPLE 1: PREPARATION OF 2-[2-(TERT-BUTYLAMINO)ETHYLSULFANYL]ETHANOL 1.7 of sodium methylate were dissolved in 15 ml dry ethanol. Mercaptoethanol was added to the solution under stirring. After completion of the mixing, the mixture was stirred for 15 more minutes, A solution of 2.5 g 2-chloro-N-tert-butylethylamine hydrochloride dissolved in 50 ml dry ethanol was added dropwise to maintain a temperature in the range of 35 to 40° C. After completion of the mixing process, the resulting suspension was heated to 75° C. and stirred for another 90 minutes, After stirring overnight at room temperature, the suspension was filtered and the filtrate was evaporated at 90° C. and 60 mbar in a rotary evaporator.

2.5 g of 2-[2-(tert-butylamino)ethylsulfanyl]ethanol were obtained, The yield was calculated to be 97%. The structure of the compound was confirmed by $^1$H-NMR.

EXAMPLE 2: COMPARISON OF PROPERTIES OF 2-[2-(TERT-BUTYLAMINO)ETHYLSULFA-NYL]ETHANOL (TBAESE) AND 2-[2-(TERT-BUTYLAMINO)ETHOXY]ETHANOL (TBAEE)

a) Thermal Stability

The thermal stability of TBAESE, was compared to TBAEE and MDEA with and without acid gas loading.

A cylinder (10 mL) was initially charged with the respective solution (8 mL) and the cylinder was closed. The cylinder was heated to 150° C. for 125 h. In the experiments conducted under acid gas loading, the acid gas loading of the solutions was 20 $Nm^3/t_{solvent}$ of $CO_2$ and 20 $Nm^3/t_{solvent}$ of $H_2S$. The decomposition level of the amines was calculated from the amine concentration measured by gas chromatography before and after the experiment. The results are shown in the Table 1.

TABLE 1

| Aqueous Solution | Ratio of Degradation | |
|---|---|---|
| | Without Acid Gas Loading | With Acid Gas Loading |
| 40 wt.-% MDEA + 60 wt.-% $H_2O$* | 0.98 | 0.89 |
| 30 wt.-% TBAEE + 70 wt.-% $H_2O$* | 0.99 | 0.92 |
| 20 wt.-% TBAESE + 75 wt.-% $H_2O$ | 0.99 | 0.96 |

*comparative example

It is evident that TBAESE have a higher thermal stability than MDEA and TBAEE in aqueous solutions in the presence of acid gas loading.

b) Acid Gas Loading and Regeneration

The $pK_a$-values for TBAESE and TBAEE were measured in the temperature range between 20° C. and 120° C. The results are shown in FIG. 1. For that an aqueous solution of the amine with a concentration of 0.01 mol/l was 50% neutralized by 0,005 mol/l HCl solution. So, the measured pH of the 50% neutralized amine solution is equal to the pKa value of the amine. The measurement was performed in a glass vessel pressurized with nitrogen to avoid any water and solvent loss.

It can be seen that the $pK_a$-values of TBAESE and TBAEE are comparable over the measured range and significantly higher than the pKa value of M DEA. From these measurements it can be concluded that the acid gas loading and the regeneration of TBAESE is comparable to TBAEE.

In summary, while TBAESE and TBAEE have similar absorption properties, TBAESE shows slightly improved thermal stability. This allows TBAESE to be handled under slightly higher regeneration temperatures, allowing more complete regeneration of the absorbent. Further TBAESE combines the benefits of sterically hindered amines, such a high selectivity for $H_2S$, and thioalcohols, a high removal rate of the sulfur compounds which may be present in the feed gas, in particular mercaptans, in a single molecule.

The invention claimed is:

1. A process for removing acid gases from a fluid stream, wherein the fluid stream is contacted with an absorbent to obtain a treated fluid stream and a laden absorbent, the absorbent comprising at least one diluent and a compound of the general formula (I)

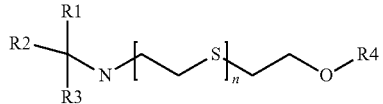

wherein R1 is $C_1$-$C_3$-alkyl; R2 is $C_1$-$C_3$-alkyl; R3 is selected from hydrogen and $C_1$-$C_3$-alkyl; R4 is selected from hydrogen and $C_1$-$C_3$-alkyl and n is an integer in the range of 1 to 4.

2. The process according to claim 1, wherein each of R1, R2 and R3 are $C_1$-alkyl.

3. The process according to claim 1, wherein the compound of general formula (I) is 2-[2-(tert-butylamino)ethylsulfanyl]ethanol.

4. The process according to claim 1, wherein the at least one diluent comprises water.

5. The process according to claim 4, wherein the absorbent additionally comprises an acid.

6. The process according to claim 1, wherein the at least one diluent comprises a non-aqueous organic solvent.

7. The process according to claim 6, wherein the organic solvent is selected from $C_{4-10}$ alcohols, ketones, esters, lactones, amides, lactams, sulfones, sulfoxides, glycols, polyalkylene glycols, di- or mono ($C_1$-$C_4$ alkyl ether) glycols, di- or mono ($C_{1-4}$-alkyl ether) polyalkylene glycols, cyclic ureas, thioalkanols and mixtures thereof.

8. The process according to claim 1, wherein the absorbent comprises at least one activator selected from a sterically unhindered primary amine and/or a sterically unhindered secondary amine.

9. The process according to claim 8, wherein the at least one activator is piperazine.

10. The process according to claim 1, wherein the acid gases comprise hydrogen sulfide and the fluid stream comprises carbon dioxide and hydrogen sulfide.

11. The process according to claim 1, wherein the laden absorbent is regenerated by means of at least one of the measures of heating, decompressing and stripping with an inert fluid.

* * * * *